United States Patent [19]

Ogasawara

[11] Patent Number: 5,731,464
[45] Date of Patent: Mar. 24, 1998

[54] PROCESS FOR PREPARATION OF INDENOL

[75] Inventor: Kunio Ogasawara, Miyagiken, Japan

[73] Assignee: Chisso Corporation, Miyagiken, Japan

[21] Appl. No.: 647,854

[22] Filed: May 15, 1996

[30] Foreign Application Priority Data

Jun. 6, 1995 [JP] Japan ................................. 7-164748

[51] Int. Cl.$^6$ ..................... C07C 211/38; C07D 303/06
[52] U.S. Cl. ............................. 564/428; 552/1; 549/545
[58] Field of Search .......................... 552/1; 549/545; 564/428

[56] References Cited

PUBLICATIONS

Ito, Satoru, et al: "Preparation of Chiral Allylic Alcohols Using *Rhizopus nigricans*. Use of the Harada–Nakanishi exciton Chirality Method for Varifying Configurational Assignments of Allylic Alcohols". Can J. Chem, vol. 65, 1987, pp. 574–582.

Didier, Eric, et al: "Chemo–Enzymatic Synthesis of 1.2–and 1.3–Amino Alcohols and Their Use in the Enantioselective Reduction of Acetophenone and Anti–Acetophenone Oxime Methyl Ether with Borene", *Tetrahedron*, vol. 47, No. 27, 1991, pp. 4941–4958.

Takahashi, etal, *Chem Pharm Bull*, 43(9), 1585–7 (1995–Sep.).

*Primary Examiner*—José G. Dees
*Assistant Examiner*—Barbara Badio
*Attorney, Agent, or Firm*—Lowe, Price, LeBlanc & Becker

[57] ABSTRACT

The invention relates to the preparation of (1S,2R)-cis-1-aminoindan-2-ol represented by formula (IX):

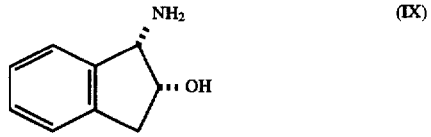

and intermediates derived therein.

5 Claims, No Drawings

PROCESS FOR PREPARATION OF INDENOL

BACKGROUND OF THE INVENTION

1. Field of the Invention

This invention relates to a process for preparation of (1S,2R)-cis-1-aminoindan-2-ol which is useful as an intermediate for a HIV-1 protease inhibitor, which in turn is useful as an AIDS therapeutic medicine, and the intermediate, as well as a process for preparation of the starting material, an optically active inden-1-ol.

2. Description of the Prior Art

Although usefulness of inden-1-ol, it is known only one preparation method of the optically active substance thereof reported by Ito and et al. (Can. J. Chem., 65, 574 (1987)). The said preparation method is to hydrolyze stereoselectively racemic 1-acetoxyindene represented by the formula (I) with use of Rhizopus nigricans bacterium. However, the description as to the optical purity and configuration thereof is not clear, which makes the report unreliable. Furthermore, although (1S,2R)-cis-1-aminoindan-2-ol which is derived from it has been reported by Didie (Tetrahedron, 47, 4941 (1991)), the preparation method cannot be said as effective.

SUMMARY OF THE INVENTION

We inventors have studied hard about these problems and found respectively that an optically active inden-1-ol can be obtained with a high optical purity and a high yield by hydrolyzing stereoselectively racemic 1-acyloxyindene expressed by the general formula (1) in the presence of lipase and that an optically active 1-acyloxyindene can be obtained by carrying out transesterification of racemic inden-1-ol stereoselectively in the presence of lipase. Furthermore, we found that (1S,2R)-cis-1-aminoindan-2-ol can be obtained effectively from an optically active 1-acyloxyindene as the starting material, to complete this invention.

As clear from the above-mentioned description, an object of the invention is to provide a process for preparation of (1S,2R)-cis-1-aminoindan-2-ol which is useful as an intermediate for a HIV-1 protease inhibitor, which in turn is useful as an AIDS therapeutic medicine, and the intermediate, as well as a process for preparation of the starting material, an optically active inden-1-ol.

This invention has the constitution of the following items (1) to (9).

(1) A process for preparation of optically active 1-acyloxyindene expressed by the following general formula (II)

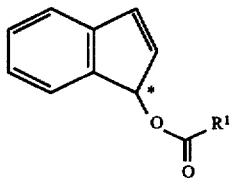

(wherein, $R^1$ denotes a straight-chain or branched alkyl group with from 1 to 20 carbon atoms) and optically active inden-1-ol expressed by the following formula (III)

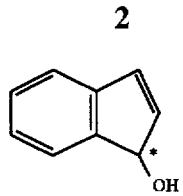

by hydrolyzing racemic 1-acyloxyindene expressed by the following formula (I)

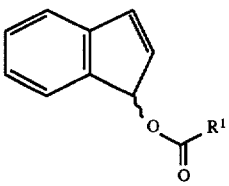

(wherein, $R^1$ denotes a straight-chain or branched alkyl group with from 1 to 20 carbon atoms) in the presence of lipase.

(2) A process for preparation of optically active 1-acyloxyindene expressed by the following general formula (II)

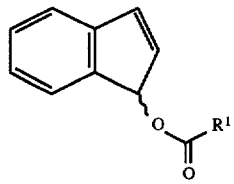

(wherein, $R^1$ denotes a straight-chain or branched alkyl group with from 1 to 20 carbon atoms) and optically active inden-1-ol expressed by the following formula (III)

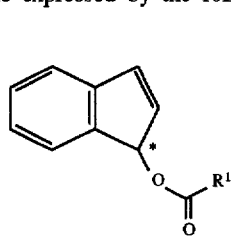

by carrying out transesterification of racemic inden-1-ol expressed by the following formula (IV)

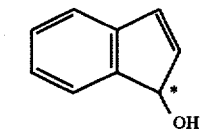

with vinyl ester in the presence of lipase.

(3) A process for preparation of (1S,2R)-cis-1-aminoindan-2-ol expressed by the following formula (IX)

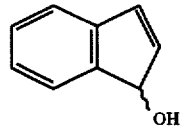

characterized in that optically active 1-acyloxyindene expressed by the general formula (II)

(wherein, R¹ denotes a straight-chain or branched alkyl group with from 1 to 20 carbon atoms) as a starting material is converted by means of a peroxide to obtain the following compounds of fomulae (V) and (VI)

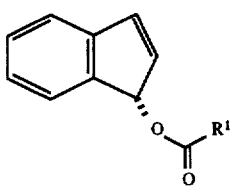

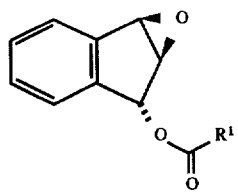

(wherein, R¹ denotes a straight-chain or branched alkyl group with from 1 to 20 carbon atoms), then one of which, that is, the compound expressed by the formula (V) is subjected to azidation to obtain the compound expressed by following general formula (VII)

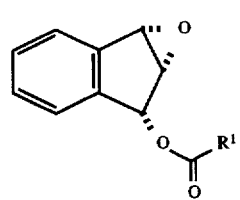

(wherein, R¹ denotes a straight-chain or branched alkyl group with from 1 to 20 carbon atoms), and then converted via the following compound of the formula (VIII)

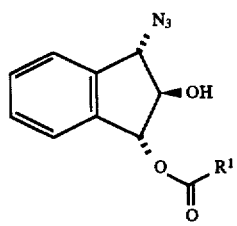

to the final product.

(4) A compound expressed by the following formula (VII)

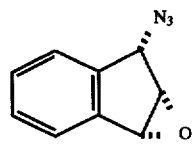

(wherein, R¹ denotes a straight-chain or branched alkyl group with from 1 to 20 carbon atoms).

(5) A compound expressed by the following formula (X)

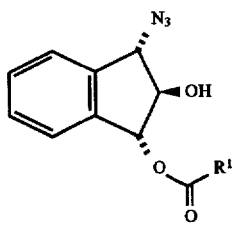

(wherein, R¹ denotes a straight-chain or branched alkyl group with from 1 to 20 carbon atoms, R² denotes one of various sulfonyl groups such as methanesufonyl group, benzenesulfonyl group and paratoluenesulfonyl etc.).

(6) A compound expressed by the following formula (XI)

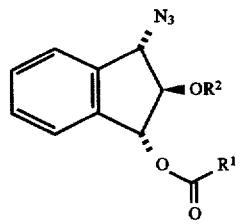

(wherein, R² denotes one of various sulfonyl groups such as methanesufonyl group, benzenesulfonyl group and paratoluenesulfonyl etc.).

(7) A compound expressed by the following formula (VIII)

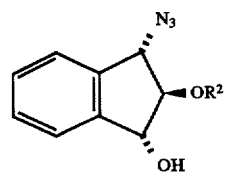

(8) A process according to the above-mentioned (1) for obtaining optically active 1-acyloxyindene expressed by the general formula (II) and optically active inden-1-ol expressed by the following formula (III), in which lipase is derived from Pseudomonas bacterium.

(9) A process according to the above-mentioned (2) for obtaining optically active 1-acytoxyindene expressed by the general formula (II) and optically active inden-1-ol expressed by the following formula (III), in which lipase is derived from Pseudomonas bacterium.

DETAILED DESCRIPTION OF THE INVENTION

The constitution and effect of the invention will be described as follows.

That is, the objective optically active 1-acyloxyindene and optically active inden-1-ol are obtained by mixing racemic 1-acyloxyindene into an aqueous solvent and stirring in the presence of lipase. The reaction temperature is suitably from 0° to 200° C., preferably from 20° to 40° C. The reaction time is from 1 to 1000 hours, preferably from 24 to 48 hours. 1-Acyloxyindene used can be obtained easily by acylating racemic inden-1-ol by a conventional method (for example, a method such as condensation with acid chloride under a basic condition may be mentioned).

As 1-acyloxyindenes, 1-acetyloxyindene, 1-propionyloxyindene, 1-butyryloxyindene, 1-pentanoyloxyindene, 1-hexanoyloxyindene etc. may be mentioned, wherein the kind of aliphatic acid being irrespective, and 1-acetyloxyindene is preferable. As the aqueous solvent, any one can be used unless it inhibits the said reaction, and there may be mentioned water, water-acetone mixed solution, phosphate buffer-acetone mixed solution etc., and 0.1M-phosphate-acetone mixed solution (9:1 V/V) is preferably used in particular. pH is suitably from 2 to 12, preferably from 7 to 8.

Furthermore, any lipase from any origin can be utilized if it has a catalytic ability for the said reaction, and there may be mentioned for example those derived from animals such as pig pancreas and pig liver, or those derived from bacteria such as Pseudomonas bacterium, Candida bacterium, Mucor bacterium, Alcaligenes bacterium, Rhizopus bacterium etc., preferably those derived from Pseudomonas bacterium. After the end of the reaction, lipase can be separated easily by a filtering operation etc. and can be reused. 1-acyloxyindene and inden-1-ol obtained by an extracting operation etc. from the aqueous solvent can be separated for example by column chromatography but can be also separated by distillation.

Furthermore, the objective optically active 1-acyloxyindene and optically active inden-1-ol are obtained by dissolving racemic inden-1-ol and vinyl ester into an organic solvent, adding lipase and stirring them. The reaction temperature is suitably from 0° to 200° C., preferably from 20° to 40° C. The reaction time is from 1 hour to 30 days, preferably from 5 to 10 days.

As vinyl esters, there may be mentioned vinyl acetate, vinyl propionate, vinyl butyrate, vinyl valerate, vinyl caproate, vinyl laurate etc., preferably vinyl acetate. As the organic solvent, any one can be used unless it inhibits the said reaction and there may be mentioned hydrocarbons such as hexane and heptane etc., aromatics such as benzene and toluene etc., ethers such as diethyl ether, diisopropyl ether, t-butylmethyl ether etc., particularly t-butylmethyl ether being preferable.

Furthermore, any lipase from any origin can be utilized if it has a catalytic ability for the said reaction and there may be mentioned for example those derived from animals such as pig pancreas and pig liver, or those derived from bacteria such as Pseudomonas bacterium, Candida bacterium, Mucor bacterium, Alcaligenes bacterium, Rhizopus bacterium etc., preferably those derived from Pseudomonas bacterium.

After the end of the reaction, lipase can be separated easily by a filtering operation etc. and can be reused. 1-acyloxyindene and inden-1-ol obtained can be separated for example by column chromatography but can be also separated by distillation.

Furthermore, optically active inden-1-ol can be derived from optically active 1-acyloxyindene by means of the conventional hydrolyzing operation (being reacted under an acidic or basic condition in the presence of water).

Next, a method for preparation of (1S,2R)-cis-1-aminoindan-2-ol will be explained. The summary thereof is shown in the following reaction formulae.

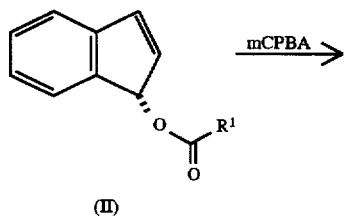

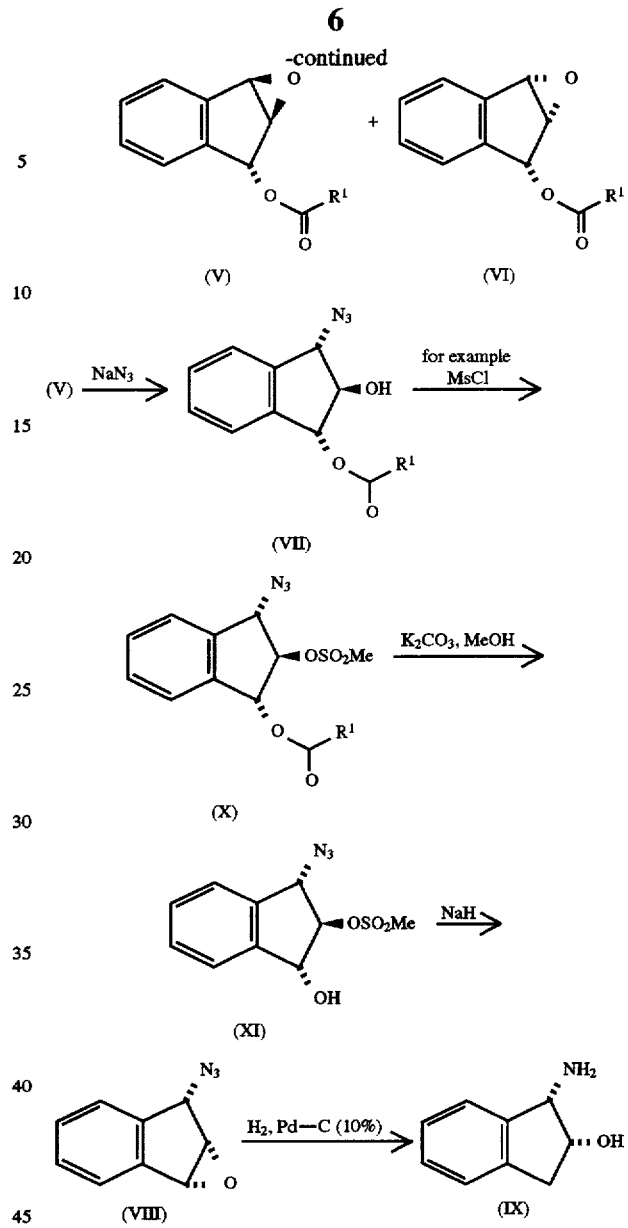

Optically active 1-acyloxyindene is subjected to epoxidation by means of a peroxide such as meta-chlorobenzoic acid etc., to obtain epoxides expressed by the formulae (V) and (VI). If epoxidation is carried out by the method of Sharpless and et al. (for example, Chem. Rev., 94, 625 (1994)), inden-1-ol is decomposed. Then, anti form (V) is reacted with metallic azide, to obtain acyloxyazide (VII) stereoselectively. As metallic azide, sodium azide is preferable. Furthermore, as to reaction conditions, it is preferable to heat at 80° C. for 2 hours in the presence of an equivalent ammonium chloride in an aqueous N,N-dimethylformamide (8:1 V/V).

Acyloxyazide (VII) is converted to sulfonate (X) by sulfonating hydroxide group in the presence of a base followed by the conventional alcoholysis. As sulfonating agents, there may be mentioned methanesulfonyl chloride, para-toluenesulfonyl chloride, benzenesulfonyl chloride etc., preferably methanesulfonyl chloride, and as the bases, there may be mentioned triethyl amine, pyridine etc. As alcohols used for alcoholysis, there may be mentioned methanol, ethanol, propanol etc., preferably methanol.

Sulfonate (X) can be converted easily to epoxy form (XI) in the presence of a base. As the bases, there may be mentioned for example lithium hydride, sodium hydride etc., preferably sodium hydride. Epoxy form (XI) can produce cis-1-aminoindan-2-ol (VIII) by hydrogenation in the conventional method. As catalysts for hydrogenation, there may be mentioned palladium-carbon system, preferably 10%-palladium-carbon.

$[\alpha]D31$-225.5° (c=0.10, CHCl$_3$), optical purity: >99% ee

Examples 2 to 8

The method similar to Example 1 was carried out with varying the kind of lipase, varying the added amount of lipase and varying reaction time as shown in Table 1.

TABLE 1

| Example | Lipase, Origin (mg/mmol of 1-Acetoxyindene) | Reaction Time (h) | (R)-inden-1-ol Yield (%): ee (%) | (S)-1-Acetoxyindene Yield (%): ee (%) |
|---|---|---|---|---|
| 2 | MY(100), *Candida cylindracea* | 2 | 11:88 | 67:17 |
| 3 | OF(100), *Candida rugosa* | 2 | 25:75 | 51:46 |
| 4 | AY(100), *Candida rugosa* | 2 | 12:87 | 64:22 |
| 5 | PPL(100), *Porcin pancreas* | 2 | 3:85 | 75:7 |
| 6 | PS(100), *Pseudomonas sp.* | 2 | 28:97 | 47:63 |
| 7 | PS(10), *Pseudomonas sp.* | 3 | 20:>99 | 58:39 |
| 8 | PS(10), *Pseudomonas sp.* | 24 | 29:98 | 42:86 |

By the above-mentioned methods, (1S,2R)-cis-1-aminoindan-2-ol can be obtained.

[Advantage of the Invention]

According to the invention, optically active 1-acyloxyindene and inden-1-ol can be obtained effectively.

Furthermore, by using the obtained optically active 1-acyloxyindene as the starting substance, (1S,2R)-cis-1-aminoindan-2-ol can be obtained, which is useful as an intermediate for a HIV-1 protease inhibitor, such as L-735, 524 (Tetrahedron Lett., 36, 2195 (1995)) or L-754,394 (Tetrahedron Lett., 35, 9355 (1994)), which in turn being useful as an AIDS therapeutic medicine.

[EXAMPLES]

The invention is explained in more detail by the following examples. Here, the invention is not limited by these examples.

Example 1

Hydrolysis of 1-acetoxyindene 1.0 g (5.75 mmol) of racemic 1-acetoxyindene and 57.5 mg of lipase PS (made by Amano Seiyaku Sha, derived from Pseudomonas bacterium) were suspended in 58 ml of phosphate buffer (0.1M)-acetone mixed solution (9:1 V/V) and stirred at 37° C. for 48 hours. The reaction solution was filtered on Celite to remove lipase. The liltrate was extracted with diethyl ether and the extracted solution was dried on magnesium sulfate. The solvent was removed under a reduced pressure and the residue was subjected to silica gel column chromatography (eluate:ethyl acetate-hexane, 1:10 V/V) to separate into 446 mg (yield 44.6%) of (S)-1-acetoxyindene and 350 mg (yield 46.1%) of (R)-inden-1-ol respectively. The specific rotations and optical purities thereof were as shown below. The optical purities were determined by high speed liquid chromatography (column: chiral cell OD, eluate: isopropanol-hexane, 1% V/V).

(S)-1-acetoxyindene $[\alpha]D25$+82.3° (c=0.21, CHCl$_3$), optical purity: >94% ee (R)-inden-1-ol As to lipase, MY and OF were made by Meito Sangyo, AY and PS were made by Amano Seiyaku, PPL was made by Sigma, and optical purities were determined by an analysis according to high speed liquid chromatography (column: chiral cell OD, eluate: isopropanol-hexane, 1% V/V or 3% V/V).

Example 9

Optical resolution of inden-1-ol by transesterification 100 mg (0.76 mmol) of racemic inden-1-ol, 0.13 mg (1.15 mmol) of vinyl acetate and 75.6 mg (100 mg of racemate/mmol) of lipase PS were suspended in 10 ml of t-butylmethyl ether and stirred at 37° C. for 7 days. After the end of the reaction, the suspension was filtered off to remove lipase. The filtrate was concentrated and the residue was subjected to silica gel column chromatography (eluate: ethyl acetate-hexane, 1:10 V/V), to separate into 50 mg (yield 38.0%, optical purity 22% ee) of (R)-1-acetoxyindene and 10 mg (yield 10.0%, optical yield 22% ee) of (S)-inden-1-ol respectively. The optical purities were determined by an analysis according to high speed liquid chromatography (column: chiral cell OD, eluate: isopropanol-hexane, 1% V/V).

Example 10

Epoxidation of (S)-1-acetoxyindene 1.80 g (10.3 mmol, >99% ee) of (S)-1-acetoxyindene and 2.61 g (31.0 mmol) of sodium hydrogen carbonate were suspended in 150 ml of dichloromethane, to which 3.83 g (15.5 mmol) of meta-chloroperbenzoic acid was added gradually at 0° C. After the addition, they were stirred further for 24 hours. The reaction was completed by adding a saturated aqueous solution of sodium hydrogen carbonate, and an organic layer was separated. The organic layer was washed with saturated saline and thereafter dried on magnesium sulfate.

After filtering off magnesium sulfate, the solvent was distilled off under a reduced pressure, and the residue was dissolved in diethyl ether. The diethyl ether layer was washed with 2% aqueous solution of sodium hydride and saturated saline in order, and dried on magnasium sulfate.

After filtering off magnesium sulfate, the solvent was distilled off under a reduced pressure. The residue was subjected to silica gel column chromatography (eluate: ethyl acetate-hexane, 1:9 V/V), to obtain 784 mg (yield 39.9%) of (1R, 2S, 3S)-1-acetoxy-2,3-epoxyindane and 784 mg (yield 39.9%) of (1R, 2R, 3R)-1-acetoxy-2,3-epoxyindane respectively. The physical properties thereof are shown as follows.

(1R, 2S,3S)-1-acetoxy-2,3-epoxyindane

IR(film): 1743 cm-1.

1H-NMR (500 MHz, CDCl$_3$): δ 2.12 (s,3H), 4.15 (d,J=2.4 Hz), 4.33 (brs, 1H), 6.09 (s, 1H), 7.31–7.37 (m, 1H), 7.45–7.50 (m, 1H), 7.53–7.58 (m, 2H). MS m/z(%): 190 (M+), 148(100). HRMS m/z: 190.0611($C_{11}H_{10}O_3$ requires 190.0630). Anal. Calcd for $C_{11}H_{10}O_3$: C, 69.45; H, 5.30. Found: C, 69.43; H, 5.22.

(1R, 2R, 3R) -1-acetoxy-2,3-epoxyindane

IR(film): 1733 cm-1.

1H-NMR (500 MHz, CDCl$_3$): δ 2.21 (s, 3H), 4.20–4.24 (m, 2H), 6.05 (d, 1H, J=2.4 Hz), 7.28–7.37 (m, 3H), 7.48 (d, 1H, J=7.3 Hz). MS m/z (%): 190 (M+) , 148 (100). HRMS m/z: 190.0626($C_{11}H_{10}O_3$ requires 190.0630). Anal. Calcd for $C_{11}H_{10}O_3$: C, 69.45; H, 5.30. Found: C, 69.55; H, 5.31.

Example 11

Synthesis of (1R, 2R, 3S) -1-acetoxy-3-azide-2-hydroxyindane 520 mg (2.74 mmol) of (1R, 2S,3S)-1-acetoxy-2,3-epoxyindane, 890 mg (13.7 mmol) of sodium azide and 293 mg (5.47 mmol) of ammonium chloride were dissolved in 20 ml of aqueous DMF (8:1, V/V), and heated with stirring at 80° C. for 2 hours. After cooling, the reaction liquid was diluted with saturated saline and extracted with ethyl acetate. The extracted solution was washed with saturated saline, and thereafter dried on magnesium sulfate.

After filtering off magnesium sulfate, the solvent was diltilled off under a reduced pressure. The residue was subjected to silica gel column chromatography (eluate: ethyl acetate-hexane, 1:4 V/V), to obtain 623 mg (yield 97.7%) of (1R, 2R, 3S)-1-acetoxy-3-azide-2-hydroxyindane. The melting point was 53° C. The other physical properties are shown as follows.

[α]D27 +84.4° (c=0.87, CHCl$_3$),

IR(film): 3500, 2098, 1739 cm-1.

1H-NMR(500 MHz, CDCl$_3$): δ 2.23(s,3H), 3.95 (d, 1H, J=1.8 Hz), 4.40 (ddd, 1H, J=6.15, 1.8 Hz), 4.76 (d, 1H, J=6.1 Hz), 5.76 (d, 1H, J=5.5 Hz), 7.35 (d, 1H, J=7.3 Hz), 7.38–7.46 (m, 3H).

MS m/z (%): 173 (M+—60), 43 (100). HRMS m/z: 173.0605 ($C_9H_7ON_3$ requires 173.0590). Anal. Calcd for $C_{11}H_{10}O_3N_3$: C, 55.63; H, 4.76, N, 18.02. Found: C, 56.36; H, 4.83, N, 17.97.

Example 12

Synthesis of (1R, 2R, 3S) -1-acetoxy-3-azide-2-methanesulfonyloxyindane 435 mg (1.95 mmol) of (1R, 2R, 3S) -1-acetoxy-3-azide-2-hydroxyindane and 0.65 ml (4.68 mmol) of triethylamine were dissolved in 15 ml of dichloromethane, and 0.18 ml (2.34 mmol) of methanesulfonyl chloride was added dropwise. After stirring at 0° C. for 5 minutes, water was added to the reaction solution, to separate an organic layer. The organic layer was washed with saturated saline, and thereafter dried on magnesium sulfate.

After filtering off magnesium sulfate, the solvent was diltilled off under a reduced pressure. The residue was subjected to silica gel column chromatography (eluate: ethyl acetate-hexane, 1:2 V/V), to obtain 601 mg (yield 99.1%) of (1R, 2R, 3S)-1-acetoxy-3-azide-2-methanesulfonyloxyindane. The melting point was 59° C. The other physical properties are shown as follows.

[α]D29 -25.5° (c=1.05, CHCl$_3$),

IR(film): 2098, 1734 cm-1.

1H-NMR(500 MHz, CDCl$_3$): δ 2.20(s,3H), 3.19(s,3H), 4.90(d, 1H, J=5.5 Hz), 5.17(dd, 1H, J=5.5,4.9 Hz), 6.26(d, 1H, J=4.3 Hz), 7.34(d, 1H, J=7.9 Hz), 7.42–7.51 (m, 3H).

MS m/z (%): 215 (M$^+$-96), 43 (100). HRMS m/z: 215.0712 ($C_{11}H_9O_2N_3$ requires 215.0694).

Example 13

Synthesis of (1S, 2S, 3R)-1-azide-2,3-epoxyindane 530 mg (1.70 mmol) of (1R, 2R, 3S)-1-acetoxy-3-azide-2-methanesulfonyloxyindane was dissolved in 20 ml of methanol, to which 259 mg (1.87 mmol) of potassium carbonate was added at the room temperature. After stirring for 10 minutes, water was added to the reaction solution and extracted with diethyl ether. The extracted solution was washed with saturated saline, and thereafter dried on magnesium sulfate.

After filtering off magnesium sulfate, the solvent was diltilled off under a reduced pressure, to obtain 457 mg of (1R, 2R, 3S)-3-azide-1-hydroxy-2-methanesulfonyloxyindane. This was dissolved in 6 ml of THF, and 88 mg (60% oil dispersion, 2.22 mmol) of sodium hydride suspended in 2 ml of THF was added dropwise at the room temperature. After stirring at the room temperature for 30 minutes, water was added to the reaction solution, which was then extracted with diethyl ether. The extracted solution was washed with saturated saline, and thereafter dried on magnesium sulfate.

After filtering off magnesium sulfate, the solvent was diltilled off under a reduced pressure to obtain residue, which was subjected to silica gel column chromatography (eluate: ethyl acetate-hexane, 1:9 V/V) to obtain 291 mg (yield 99.7%) of (1S,2S,3R)-1-azide-2,3-epoxyindane. The melting point was 69° C. The other physical properties are shown as follows.

[α]D29 -360.2° (c=0.17, CHCl$_3$),

IR(film): 2094 cm-1.

1H-NMR (500 MHz, CDCl$_3$): δ 4.19(t, 1H, J=2.4 Hz), 4.22(d, 1H, J=2.4 Hz), 4.54 (brd, 1H, J=2.4 Hz) , 7.30–7.43 (m, 3H), 7.51 (d, 1H, J=7.3 Hz).

MS m/z (%): 173 (M+), 131 (100). HRMS m/z: 173.0579 ($C_9H_7ON_3$ requires 173.0589).

Example 14

Synthesis of cis-(1S, 2R) -1-aminoindan-1-ol 100 mg (0.58 mmol) of (1S, 2S, 3R)-1-azide-2,3-epoxyindane was dissolved in 10 ml of ethanol (containing 0.3 ml of chloroform), into which 15 mg of 10%-palladium-carbon was suspended, and then stirred at the room temperature for 6 hours under a hydrogen atmosphere of 3 kg/cm$^2$. After filtering off the catalyst, the solvent of the filtrate was distilled off under a reduced pressure, to obtain hydrochloride of cis-(1S,2R)-1-aminoindan-2-ol. The solution was made alkaline by adding 5% aqueous sodium hydroxide solution, and extracted with dichloromethane.

The dichloromethane layer was dried on magnesium sulfate, and the solvent was distilled off under a reduced pressure after filtering off magnesium sulfate.

The residue was recrystallized with dichloromethane-hexane mixed solvent, to obtain 59 mg (yield 69.0%) of cis-(1S,2R)-1-aminoindan-2-ol. The melting point was 105° C. The other physical properties are shown as follows.

[α]D31-62.0° (c=0.90, CHCl$_3$).

IR(film): 3336 cm-1.

1H-NMR (500 MHz, CDCl$_3$): δ 2.22 (brs, 3H), 2.95 (dd, 1H, J=16.5, 3.1 Hz), 3.10 (dd, 1H, J=16.5, 5.5 Hz), 4.32 (brd, 1H, J=4.9 Hz), 4.36–4.41 (m, 1H), 7.22–7.32 (m, 4H).

MS m/z (%): 149 (M$^+$), 104 (100). HRMS m/z: 149.0828 (C$_9$H$_7$ON$_3$ requires 149.0841).

What I claim is:

1. A process for the preparation of an (1S, 2R)-cis-1-aminoindan-2-ol represented by formula (IX)

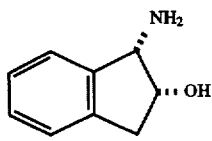
(IX)

comprising the steps of:
epoxidizing an optically active 1-acyloxyindene represented by formula (II) in the presence of metachloroperbenzoic acid to obtain compounds represented by formulae (V) and (VI);

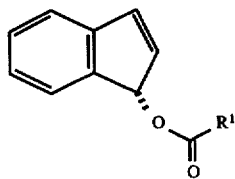
(II)

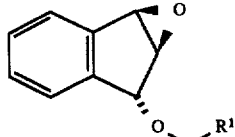
(V)

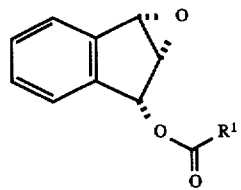
(VI)

azidating the compound represented by formula (V) in the presence of a metallic azide to obtain a compound represented by formula (VII);

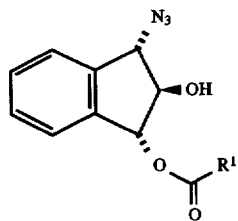
(VII)

epoxidizing the compound represented by formula (VII) in the presence of a base to obtain a compound represented by formula (VIII);

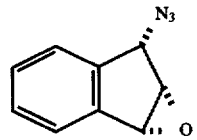
(VIII)

and, hydrogenating the compound represented by formula (VIII) to obtain a compound represented by the formula (IX), wherein R$^1$ is a straight-chain or branched alkyl group having from 1 to 20 carbon atoms.

2. A compound represented by formula (VII)

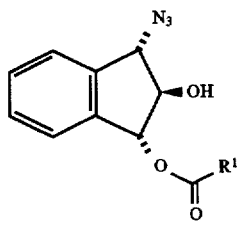
(VII)

wherein, R$^1$ denotes a straight-chain or branched alkyl group having 1 to 20 carbon atoms.

3. A compound represented by formula (X)

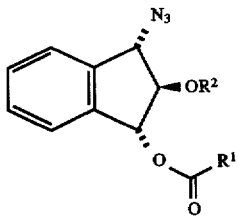
(X)

wherein, R$^1$ denotes a straight-chain or branched alkyl group having 1 to 20 carbon atoms, and R$^2$ denotes a sulfonyl group.

4. A compound represented by formula (XI)

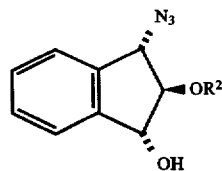
(XI)

wherein, R$^2$ denotes a sulfonyl group.

5. A compound represented by formula (VIII)

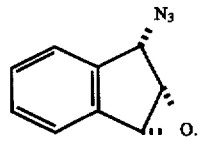
(VIII)

* * * * *